United States Patent [19]

Juby

[11] 4,209,620
[45] Jun. 24, 1980

[54] SUBSTITUTED 3-(1H-TETRAZOL-5-YL)-4H-PYRIDO[1,2-A]PYRIMIDIN-4-ONE DERIVATIVES HAVING ANTIALLERGY ACTIVITY

[75] Inventor: Peter F. Juby, Jamesville, N.Y.

[73] Assignee: Bristol-Myers Company, New York, N.Y.

[21] Appl. No.: 951,437

[22] Filed: Oct. 16, 1978

Related U.S. Application Data

[60] Continuation-in-part of Ser. No. 916,440, Jun. 19, 1978, abandoned, which is a division of Ser. No. 800,264, May 25, 1977, Pat. No. 4,122,274.

[51] Int. Cl.$^2$ .................. A61K 31/505; C07D 239/70; C07D 491/04
[52] U.S. Cl. .................... 544/252; 424/251; 544/250
[58] Field of Search ................. 544/252, 250

[56] References Cited

U.S. PATENT DOCUMENTS

| 3,960,863 | 6/1976 | Sato et al. | 544/282 |
| 3,965,100 | 6/1976 | Yale | 544/252 |
| 4,014,881 | 3/1977 | Kadin et al. | 544/252 |
| 4,017,625 | 4/1977 | Kadin | 544/252 |
| 4,022,897 | 5/1977 | Yale | 544/282 |
| 4,083,980 | 4/1978 | Schromm et al. | 544/250 |
| 4,127,720 | 11/1978 | Juby et al. | 544/252 |

FOREIGN PATENT DOCUMENTS 2513930 10/1975 Fed. Rep. of Germany ........... 544/252

OTHER PUBLICATIONS

Gupta, et al., "Indian Journal Chemistry", vol. 9, 1971, pp. 201–206.

*Primary Examiner*—Donald G. Daus
*Assistant Examiner*—James H. Turnipseed
*Attorney, Agent, or Firm*—David M. Morse

[57] ABSTRACT

A novel series of substituted 3-(1H-tetrazol-5-yl)-4H-pyrido[1,2-a]pyrimidin-4-ones is provided for use as inhibitors of allergic reactions. The compounds exhibit antiallergy activity by both oral and parenteral routes of administration.

13 Claims, No Drawings

SUBSTITUTED 3-(1H-TETRAZOL-5-YL)-4H-PYRIDO[1,2-A]PYRIMIDIN-4-ONE DERIVATIVES HAVING ANTIALLERGY ACTIVITY

CROSS-REFERENCE TO RELATED APPLICATION

This application is a continuation-in-part application of co-pending application Ser. No. 916,440 filed June 19, 1978, now abandoned, which in turn is a division of application Ser. No. 800,264 filed May 25, 1977, now U.S. Pat. No. 4,122,274.

BACKGROUND OF THE INVENTION

1. Field of the Invention

This invention relates to substituted 3-(1H-tetrazol-5-yl)-4H-pyrido[1,2-a]pyrimidin-4-one derivatives and to their use as inhibitors of allergic reactions.

2. Description of the Prior Art

Various medicinal agents have been employed in the treatment of allergic reactions such as bronchial asthma and allergic rhinitis which are believed to result mainly from antigen-antibody interaction. With respect to bronchial asthma, one of the most serious of these allergically-mediated diseases, bronchodilators such as theophylline, isoproterenol, epinephrine and atropine are used primarily in providing symptomatic relief. These agents, however, have undesirable side effects, e.g. cardiac stimulation and gastrointestinal distress.

With the recent introduction of disodium cromoglycate described by J. S. G. Cox, et al. in *Adv. in Drug Res.*, 5, 115–196 (1970), the physician has been provided with an agent which, when administered to asthmatic patients prior to inhalation of specific antigens, inhibits the release of mediators, e.g. histamine and SRS-A (slow-reacting-substance of anaphylaxis), believed to be responsible for the asthmatic response. While making possible a prophylactic treatment for bronchial asthma without cardiovascular side effects and thus representing a significant advance, disodium cromoglycate suffers from a major disadvantage in that it is not orally absorbed and must be administered by inhalation.

With respect to the compounds of the present invention, no examples of tetrazol-5-yl-4H-pyrido[1,2-a]pyrimidin-4-ones have been found in the literature. Numerous examples of the pyrido[1,2-a]pyrimidine ring system, however, are known, including many 4-oxo derivatives.

U.S. Pat. No. 3,585,198 reviews some of the literature of the pyrido[1,2-a]pyrimidines and discloses compounds of the general formula

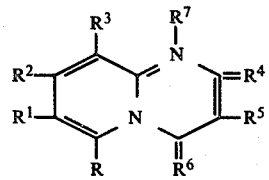

where R, $R^1$, $R^2$ and $R^3$ may be hydrogen, alkyl, alkoxy, halogen, nitro or amino, $R^4$ is hydrogen, alkyl, aralkyl, aryl, =O, alkoxy, halogen or hydroxy, $R^5$ is hydrogen, halogen, a —CH₂—OH group, a carboxylic acid or carboxylic acid derivative group, $R^6$ is hydrogen, alkyl, aralkyl, aryl, =O, alkoxy, halogen or hydroxy and $R^7$ is hydrogen, alkyl, aryl or alkyl. The disclosed compounds are said to exhibit analgesic, antipyretic and narcosis potentiating effects.

U.S. Pat. No. 3,929,787 discloses 2-aryl-9-alkyl-4H-pyrido[1,2-a]pyrimidin-4-one compounds of the formula

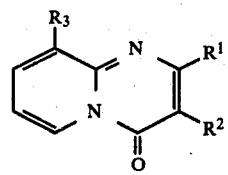

where $R^1$ is phenyl or substituted phenyl, $R^2$ is hydrogen or alkyl and $R^3$ is alkyl. These compounds are reported to be intermediates in preparing the corresponding 6,7,8,9-tetrahydro derivatives which possess central nervous system depressant activity.

U.S. Pat. No. 3,072,485 discloses inter alia compounds of the formula

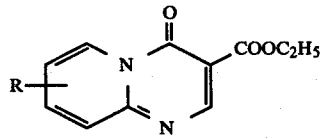

where R is hydrogen, bromo, chloro, iodo or methyl. The compounds are used as photographic sensitizers.

Compounds of the formula

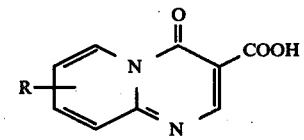

where R is hydrogen, 9-methyl or 8-methyl are disclosed by Okamoto, et al. in Chem. Pharm. Bull. (Tokyo), 22, 243 (1974). NO pharmacological utility for the compounds is indicated.

U.S. Pat. No. 3,960,847 discloses inter alia 9-substituted pyrido[1,2-a]pyrimidines of the formula

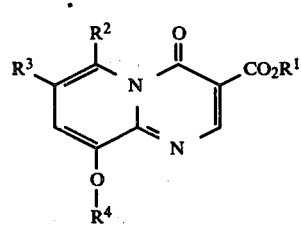

where $R^1$ is hydrogen or $C_1$-$C_4$ alkyl, $R^2$ and $R^3$ are hydrogen, $C_1$-$C_4$ alkyl, $CF_3$, F, Cl or Br and $R^4$ is inter alia an alkyl radical substituted by a phenyl or substituted phenyl radical, such as benzyl, substituted benzyl, phenethyl or substituted phenethyl. The compounds are said to have both central nervous system and hypotensive activities.

J. K. Landquist has described in *J. Chem. Soc.* (C), 2735 (1971) the preparation of the carboxamide compound of the formula

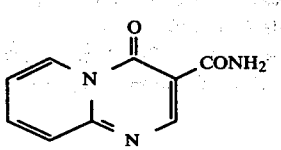

by treatment of the corresponding ethyl ester with ammonium hydroxide in ethanol. No pharmacological utility is given for the disclosed carboxamide.

Preparation of the cyano derivatives of the formula

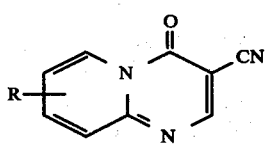

where R is hydrogen, 6-methyl or 9-methyl is disclosed in *J. Amer. Chem. Soc.*, 80, 3066 (1958). No pharmacological utility for the compounds is indicated.

Other references to the chemistry of pyrido[1,2-a]-pyrimidinones include *J. Amer. Chem. Soc.*, 74, 5491 (1952), *J. Org. Chem.*, 33, 3015 (1968), *Arzneim.-Forsch.*, 22, 815 (1972) and Tetrahedron Lett., (12), 1019 (1975).

SUMMARY OF THE INVENTION

This invention relates to new therapeutically useful 3-(1H-tetrazol-5-yl)-4H-pyrido[1,2-a]pyrimidin-4-one derivatives, to processes for their preparation, to pharmaceutical compositions containing them and to methods for treating allergically-mediated diseases in mammals by administration of such derivatives or pharmaceutical compositions thereof. The compounds and compositions provided by the present invention are particularly valuable in the prophylactic treatment of allergic bronchial asthma by oral administration.

The antiallergy agents of the present invention may be represented by the formula

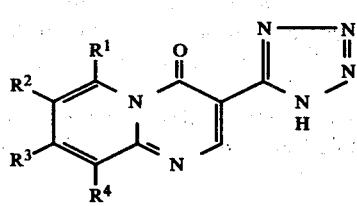

wherein $R^2$ and $R^3$ or $R^3$ and $R^4$ when taken together are methylenedioxy or

in which n is 3, 4 or 5 and the remaining available $R^1$, $R^2$ and $R^4$ substituents are each independently hydrogen, halogen, (lower)alkyl, cyclo(lower)alkyl, cyclo(-lower)alkyl(lower)alkyl, (lower)-alkenyl, (lower)alkynyl, (lower)alkoxy, (lower)alkoxy(lower)alkyl, —O-(lower)alkenyl,

in which m is 0 or an integer from 1 to 6 and n is an integer from 2 to 7, —OCH$_2$(CH$_2$)$_x$O(CH$_2$)$_y$CH$_3$ in which x and y are each independently 0 or an integer from 1 to 6, CF$_3$, hydroxy, hydroxymethyl, (lower)alkylthio, amino, nitro,

in which r is 4 or 5, (lower)alkylamino, di(lower)alkylamino, carboxyl, —CO$_2$-(lower)alkyl, phenyl, phenyl substituted by one or two (lower)alkyl, (lower)alkoxy or halogen radicals, benzyl, (lower)alkylsulfinyl, $R^c$—CO— in which $R^c$ is (lower)alkyl, $R^c$—COO— in which $R^c$ is (lower)alkyl, —O(CH$_2$)$_k$OH in which k is an integer from 2 to 6,

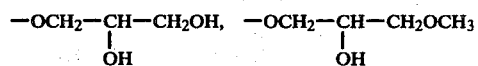

or —OCH$_2$C$_6$H$_5$, with the proviso that $R^1$ and $R^2$ may not both be tertiary alkyl or tertiary alkoxy groups.

The $R^1$, $R^2$ or $R^4$ substituent groups disclosed above may be further defined as follows:

(a) Halogen includes chlorine, bromine, fluorine and iodine;

(b) (Lower)alkyl includes both straight and branched chain saturated aliphatic hydrocarbon radicals having from 1-6 carbon atoms inclusive, e.g. methyl, ethyl, n-propyl, isopropyl, n-butyl, isobutyl, sec-butyl, tert-butyl, n-pentyl, isopentyl, n-hexyl, etc.;

(c) (Lower)alkenyl includes straight or branched unsaturated aliphatic hydrocarbon radicals containing one double bond and having from 2-6 carbon atoms inclusive, e.g. vinyl, allyl, isopropenyl, 2- or 3-methallyl or 3-butenyl;

(d) (Lower)alkoxy includes C$_1$-C$_6$ alkoxy radicals, the alkyl portion of such radicals being defined as in (b) above. Examples include methoxy, ethoxy, n-propoxy, isopropoxy, n-butoxy, isobutoxy, sec-butoxy, n-pentyloxy, isopentyloxy, n-hexyloxy, etc.;

(e) —O-(lower)alkenyl groups include radicals in which the alkenyl portion is as defined above in (c), e.g. vinyloxy, allyloxy or isopropenyloxy;

(f)

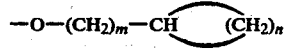

includes cyclo(lower)-alkyloxy and cyclo(lower)alkyl-(C$_1$-C$_6$)alkyloxy groups in which the cycloalkyl ring contains from 3 to 8 carbon atoms, preferably 3-6 carbon atoms. Examples of such groups are cyclopropyloxy, cyclobutyloxy, cyclopentyloxy, cyclohexyloxy, cycloheptyloxy, cyclopropylmethyloxy, cyclopropylethyloxy, cyclobutylmethyloxy, cyclobutylethyloxy, cyclopentylmethyloxy, cyclohexylmethyloxy, cyclohexylethyloxy and cyclohexylpropyloxy;

(g) —O—CH$_2$(CH$_2$)$_x$O(CH$_2$)$_y$CH$_3$ includes radicals such as —OCH$_2$OCH$_3$, —OCH$_2$CH$_2$OCH$_3$, —OCH$_2$CH$_2$OCH$_2$CH$_3$, —OCH$_2$OCH$_2$CH$_3$ and —OCH$_2$CH$_2$CH$_2$OCH$_2$CH$_3$;

(h) (Lower)alkylthio includes C$_1$-C$_6$ alkylthio radicals in which the alkyl portion is as defined above in (b). Examples of such groups are methylthio, ethylthio, n-propylthio and n-butylthio;

(i) (Lower)alkylamino includes C$_1$-C$_6$ alkylamino radicals in which alkyl is as defined in (b). Examples of such groups are methylamino, ethylamino, propylamino and butylamino;

(j) Di(lower)alkylamino includes di $C_1$-$C_6$ alkylamino radicals in which alkyl is as defined above in (b). Examples of such groups are dimethylamino and diethylamino;

(k) —$CO_2$-(Lower)alkyl includes ester radicals in which the alkyl moiety is as defined above in (b), e.g. carbomethoxy, carbethoxy, carbopropoxy and carbobutoxy;

(l) (Lower)alkylsulfinyl represents radicals of the formula

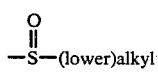

in which the alkyl portion is as defined above in (b). Examples of such radicals include methylsulfinyl, ethylsulfinyl, n-propylsulfinyl, isopropylsulfinyl, n-butylsulfinyl, sec-butylsulfinyl, isobutylsulfinyl, t-butylsulfinyl, n-pentylsulfinyl and n-hexylsulfinyl. The most preferred alkylsulfinyl group is methylsulfinyl;

(m) Acyl includes radicals of the type $R^c$—CO— where $R^c$ is an aliphatic, cycloaliphatic, aromatic or araliphatic hydrocarbon radical or a heterocyclic-aliphatic radical, e.g. $CH_3CO$—, $C_2H_5CO$—, $C_3H_7CO$—, $C_6H_5CO$—, $C_6H_5CH_2CO$—,

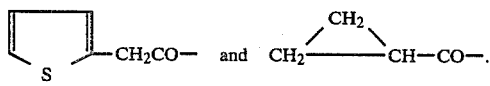

Preferred acyl groups are those in which $R^c$ is alkyl as defined in (b);

(n) Acyloxy includes radicals of the type $R^c$—COO— in which $R^c$ is as defined above in connection with acyl and is preferably $C_1$-$C_6$ alkyl. Examples are $CH_3COO$—, $C_2H_5COO$—, $C_3H_7COO$—, $C_6H_5CH_2COO$— and $C_6H_5COO$—;

(o)

includes pyrrolidino and piperidino;

(p) Cyclo(lower)alkyl means cycloalkyl radicals having from 3–6 carbon atoms. Examples include cyclopropyl, cyclobutyl, cyclohexyl, etc.;

(q) $R^2$ and $R^3$ or $R^3$ and $R^4$ taken together may be

which represents a saturated five, six or seven membered monocyclic hydrocarbon radical fused to the A ring of the pyrido[1,2-a]pyrimidine ring system, e.g.

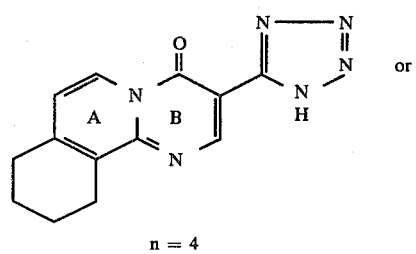

n = 4

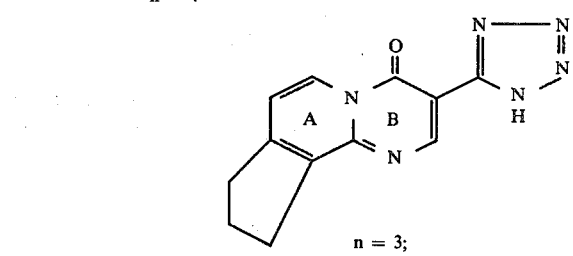

n = 3;

(r) (Lower)alkynyl represents straight or branched unsaturated aliphatic hydrocarbon radicals containing one triple bond and having from 2 to 6 carbon atoms inclusive, e.g. ethynyl, propargyl, butynyl, pentynyl or hexynyl;

(s) (Lower)alkoxy(lower)alkyl represents radicals where the (lower)alkoxy and (lower)alkyl portions are as defined above in (d) and (b), respectively, e.g. methoxymethyl, methoxyethyl, ethoxymethyl, ethoxyethyl, methoxypropyl, etc.; and (t) Cyclo(lower)alkyl(lower)alkyl represents radicals in which the cyclo(lower)alkyl and (lower)alkyl portions are as defined above in (p) and (b) respectively, e.g. cyclopropylmethyl, cyclopropylethyl, cyclopropylbutyl, cyclohexylmethyl, cyclohexylethyl, etc.

Preferred embodiments of the present invention comprise the compounds of formula I wherein:

(a) $R^2$ and $R^3$ or $R^3$ and $R^4$=methylenedioxy;

(b) $R^2$ and $R^3$ or $R^3$ and

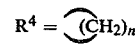

in which n is 3, 4 or 5;

(c) $R^2$ and $R^3$ or $R^3$ and $R^4$=methylenedioxy and the remaining substituents are each independently hydrogen, halogen, (lower)alkyl, (lower)-alkoxy, (lower)alkoxy(lower)alkyl, (lower)-alkylthio or di(lower)alkylamino;

(d) $R^2$ and $R^3$ or $R^3$ or

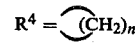

in which n is 3, 4 or 5 and the remaining substituents are each independently hydrogen, halogen, (lower)-alkyl, (lower)alkoxy, (lower)alkoxy(lower)-alkyl, (lower)alkylthio or di(lower)alkylamino; and (e) $R^3$ and

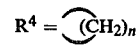

in which n is 3, 4 or 5 and $R^1$ and $R^2$ are each independently hydrogen, halogen, (lower)alkyl, (lower)alkoxy, (lower)-alkoxy(lower)alkyl, (lower)alkylthio or di(lower)alkylamino.

A more preferred embodiment of the present invention comprises the compounds of the formula

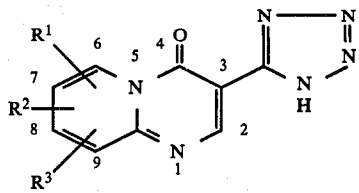

wherein any two of $R^1$, $R^2$ and $R^3$ at positions 7 and 8 or 8 and 9 of the pyrido[1,2-a]pyrimidine ring system when taken together represent methylenedioxy or

in which n is 3, 4 or 5 and the remaining available $R^1$, $R^2$ or $R^3$ substituent is hydrogen, halogen, (lower)alkyl, cyclo(lower)alkyl, cyclo(lower)alkyl(lower)alkyl, (lower)alkenyl, (lower)alkynyl, (lower)alkoxy, (lower)alkoxy(lower)alkyl, —O-(lower)alkenyl, $$-O-(CH_2)_mCH(CH_2)_n$$

in which m is O or an integer from 1 to 6 and n is an integer from 2 to 7, $-OCH_2(CH_2)_xO(CH_2)_yCH_3$ in which x and y are each independently O or an integer from 1 to 6, $CF_3$, hydroxy, hdroxymethyl, (lower)alkylthio, amino, nitro,

in which r is 4 or 5, (lower)alkylamino, di(lower)alkylamino, carboxyl, $-CO_2$-(lower)alkyl, phenyl, phenyl substituted by one or two (lower)alkyl, (lower)alkoxy or halogen radicals, benzyl, (lower)alkylsulfinyl, $R^c$-CO- in which $R^c$ is (lower)alkyl, $R^c$-COO- in which $R^c$ is (lower)alkyl, $-O(CH_2)_kOH$ in which k is an integer from 2 to 6, $$-OCH_2-CH-CH_2OH, \quad -OCH_2-CH-CH_2OCH_3$$
$$\quad\quad\quad\quad | \quad\quad\quad\quad\quad\quad\quad\quad | $$
$$\quad\quad\quad\quad OH \quad\quad\quad\quad\quad\quad\quad OH$$

or $-OCH_2C_6H_5$, or a pharmaceutically acceptable salt thereof.

Preferred embodiments encompassed by formula I' comprise the compounds wherein:

(a) two of $R^1$, $R^2$ and $R^3$ at positions 7 and 8 or 8 and 9 are methylenedioxy;

(b) two of $R^1$, $R^2$ and $R^3$ at positions 7 and 8 or 8 and 9 are methylenedioxy and the remaining $R^1$, $R^2$ or $R^3$ is hydrogen, halogen, (lower)alkyl, (lower)alkoxy, (lower)alkoxy(lower)alkyl, (lower)alkylthio or di(lower)alkylamino;

(c) two of $R^1$, $R^2$ and $R^3$ at positions 7 and 8 or 8 and 9 are

in which n is 3, 4 or 5;

(d) two of $R^1$, $R^2$ and $R^3$ at positions 7 and 8 or 8 and 9 are

in which n is 3, 4 or 5 and the remaining $R^1$, $R^2$ or $R^3$ is hydrogen, halogen, (lower)alkyl, (lower)alkoxy, (lower)alkoxy(lower)alkyl, (lower)alkylthio or di(lower)alkylamino; and (e) two of $R^1$, $R^2$ and $R^3$ at positions 8 and 9 are

in which n is 3, 4 or 5 and the remaining $R^1$, $R^2$ or $R^3$ is hydrogen, halogen, (lower)alkyl, (lower)alkoxy, (lower)alkoxy(lower)alkyl, (lower)alkylthio or di(lower)alkylamino.

Another more preferred embodiment of the present invention comprises the compounds of the formula

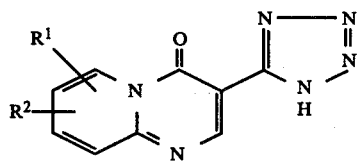

wherein $R^1$ and $R^2$ when taken together at positions 7 and 8 or 8 and 9 of the pyrido[1,2-a]pyrimidine ring system are methylenedioxy or

in which n is 3, 4 or 5, or a pharmaceutically acceptable salt thereof. A preferred group of compounds within the scope of formula I" comprises those wherein $R^1$ and $R^2$ when taken together at positions 7 and 8 or 8 and 9 are

in which n is 3, 4 or 5.

An especially preferred embodiment of the present invention comprises the compounds of the formula

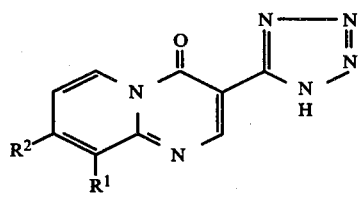

wherein $R^1$ and $R^2$ taken together at positions 8 and 9 of the pyrido[1,2-a]pyrimidine ring system are methylenedioxy or

in which n is 3, 4 or 5, or a pharmaceutically acceptable salt thereof. The preferred compounds within this group are those wherein $R^1$ and $R^2$ are

in which n is 3, 4 or 5, most particularly the compound wherein n is 4.

Since the compounds of this invention are amphoteric in nature, they can be converted to salts of either acids or bases by treating said compounds with a substantially equimolar amount of a chosen acid or base in an aqueous solution or in a suitable organic solvent such as methanol or ethanol. When such salts are to be used for human consumption, the acids or bases which are used to prepare the pharmaceutically acceptable salts must, of course, be those which necessarily form non-toxic salts. Examples of suitable acids include hydrochloric, hydrobromic, hydroiodic, nitric, sulfuric, phosphoric, acetic, lactic, citric, tartaric, oxalic, succinic, maleic, gluconic, ascorbic and p-toluene sulfonic. Pharmaceutically acceptable salts may be formed from such bases as ammonia, organic amines and metal salts, e.g. metal salts containing sodium, potassium, calcium, magnesium, barium and aluminum cations. Representative of such bases are ammonia, primary amines such as n-propylamine, n-butylamine, ethanolamine, ethylenediamine, cyclohexylamine, benzylamine, ethylamine, octylamine or tris(hydroxymethyl)aminomethane, secondary amines such as diethanolamine, tertiary amines such as triethanolamine, N-methylpyrrolidine, N-methylmorpholine, or 1,5-diazabicyclo[4,3,0]-5-nonene and metal compounds such as sodium hydroxide, potassium hydroxide, ammonium hydroxide, sodium ethoxide, potassium methoxide, magnesium hydroxide, calcium hydroxide or aluminum hydroxide.

Those skilled in the art will appreciate that the compounds represented by formulae I-I''' contain a tautomeric hydrogen atom and the compounds are thus capable of existing in the 1H-tetrazol-5-yl form (see formula $I_a$ below) and the 2H-tetrazol-5-yl form (formula $I_b$ below).

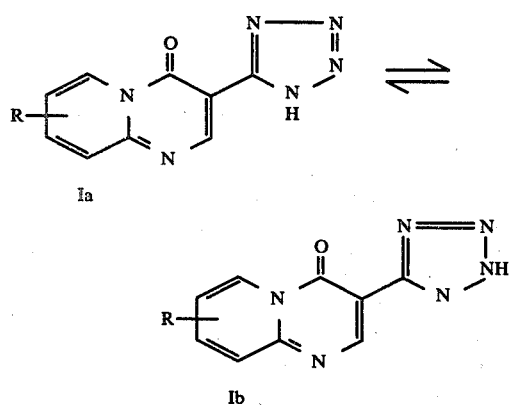

This invention embraces both forms, but for the sake of convenience, structure $I_a$ has been arbitrarily selected to describe the present compounds.

The compounds of the present invention may be prepared by the methods set forth below.

One preferred method comprises reacting a nitrile of the formula

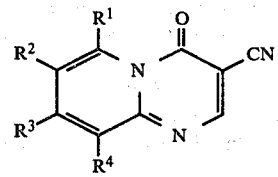

(wherein $R^1$, $R^2$, $R^3$ and $R^4$ are defined as above in reference to formula I) with an azide salt selected from the group consisting of ammonium, substituted ammonium and sodium and lithium azide in an inert organic solvent. The nitrile II and azide salt may be used in approximately equimolar amounts. The general conversion of nitriles to tetrazoles is described by W. G. Finnegan, et al. in J. Am. Chem. Soc., 80, 3908 (1958). Examples of suitable azide salts for this process are provided by Finnegan in the above-mentioned reference and include azides such as $NaN_3$, $LiN_3$, $NH_4N_3$, $(n-C_4H_9)_2NH_2N_3$, $C_6H_5NH_3N_3$ and $(CH_3)_4NN_3$. The azide salt may be added directly or may be generated in situ, e.g. by double decomposition reactions of sodium azide and an appropriate chloride salt such as LiCl, $NH_4Cl$, $(CH_3)_4NCl$, etc. While the condensation reaction proceeds over a wide temperature range, it is preferred in order to minimize reaction times to use elevated temperatures, e.g. from about 100° C. up to the reflux temperature of the solvent system. The inert organic solvent may in general be any solvent having good solvent power for the azide salt and which is chemically inert. Examples of preferred solvents are dimethylformamide, dimethylacetamide, dimethylsulfoxide and hexamethylphosphoramide. The most preferred solvent is dimethylformamide. The condensation reaction is found to be subject to general acid catalysis and yields are improved by addition of such reagents as hydrazoic acid, amine hydroazides and Lewis acids such as $BF_3$ to the sodium azide. At the completion of the reaction, the tetrazole product may be recovered from the reaction mixture by removing the solvent, diluting the residue with water and then acidifying the mixture to give the desired product of formula I. The product may be further purified by recrystallization and optionally converted to a pharmaceutically acceptable salt thereof as described above. Following condensation, products of formula I may, if desired, be further reacted by methods known per se to convert one or more $R^1$, $R^2$ or $R^4$ substituent groups to other substituent groups within the scope of formula I. Thus, for example, a compound of formula I having a nitro substituent may be subjected to catalytic hydrogenation to give the corresponding aminosubstituted compound or a compound having an amino substituent may be alkylated to give the corresponding (lower)alkylamino or di(lower)alkylamino-substituted compound.

An alternative and preferred variation of the above procedure involves condensing the nitrile starting material II with aluminum azide in tetrahydrofuran followed by an acidification recovery step as described above. The reaction may conveniently be carried out by reacting nitrile II with aluminum chloride and sodium azide in molar proportions of about 1:1:3, respectively. While the temperature for this reaction is not critical, advantageous results have been obtained at the reflux temperature of the solvent.

Another alternative variation of the above procedure comprises heating the desired nitrile compound II with either hydrazoic acid in an inert organic solvent such as benzene, xylene or toluene or with sodium azide and acetic acid in butanol. In this procedure an acidification step is not required to recover the desired end-product.

An alternative and most preferred procedure for preparing the compounds of formula I comprises reacting an acrylate intermediate of the formula

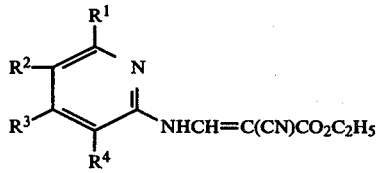

(wherein $R^1$, $R^2$, $R^3$ and $R^4$ are as defined above in reference to formula I) with aluminum azide in tetrahydrofuran. The preferred reaction conditions, i.e. molar ratios and temperature ranges, are as described above in connection with the nitrile to tetrazole conversion with $Al(N_3)_3$. The product of formula I may be conveniently recovered from the reaction mixture by addition of sufficient water followed by acidification to effect precipitation of the desired compound I. The tetrazole product I may, if desired, be subsequently converted as discussed above to a pharmaceutically acceptable salt or to another product of formula I having different $R^1$, $R^2$ or $R^4$ substituents.

Another preferred procedure for preparing the compounds of formula I comprises reacting a 2-aminopyridine of the formula

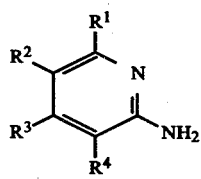

(wherein $R^1$, $R^2$, $R^3$ and $R^4$ are as defined above in reference to formula I) with ethyl ethoxymethylenecyanoacetate of the formula

$$C_2H_5CH=C(CN)CO_2C_2H_5 \quad \text{(VIII)}$$

and aluminum azide in tetrahydrofuran. Approximately equimolar quantities of the three reactants are used, and the aluminum azide may be conveniently prepared in situ by reaction of sodium azide and aluminum chloride in molar proportions of about 3:1, respectively. For best results, the reaction is carried out at the reflux temperature of the solvent. At the conclusion of the reaction, the desired product can be recovered by addition of sufficient water followed by acidification to precipitate compound I from the reaction mixture. The product may as described above be further reacted to produce a pharmaceutically acceptable salt thereof or another product of formula I having different $R^1$, $R^2$ or $R^4$ substituents.

The above process is a preferred embodiment of the present invention since it enables compound I to be prepared directly from the basic 2-aminopyridine and ethyl ethoxymethylenecyanoacetate starting materials without the necessity of first preparing and isolating one or more intermediates required for the alternative methods described above.

The nitrile starting materials of formula II may be prepared by known reaction routes. One reaction scheme is indicated below:

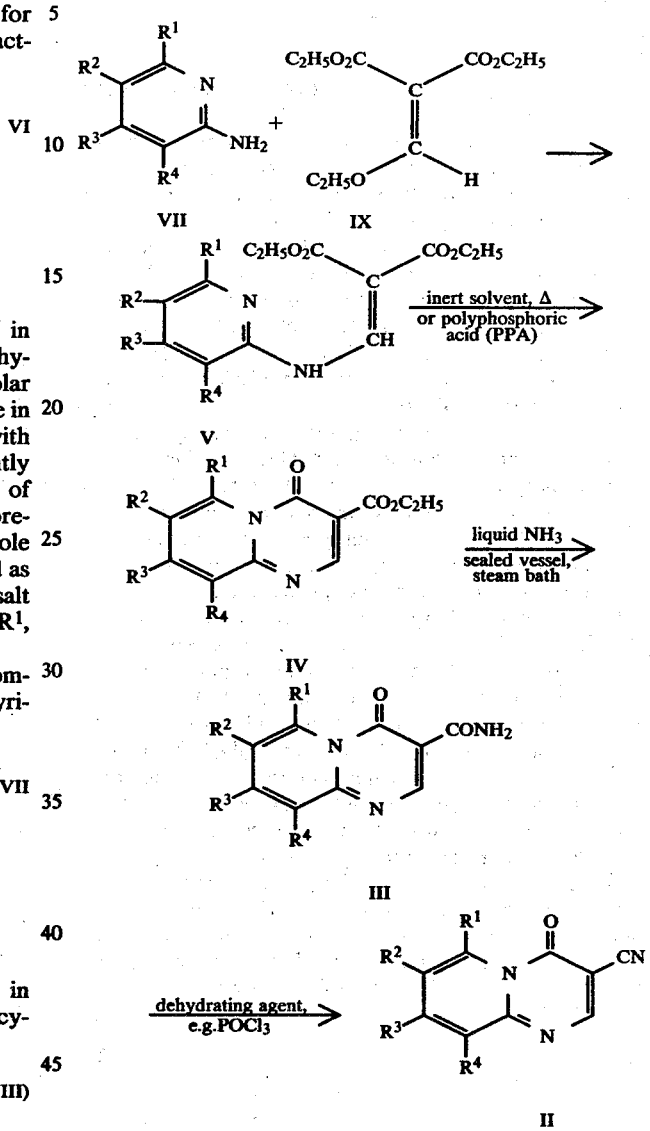

The 2-aminopyridine starting materials of formula VII are known compounds or are prepared by methods well known in the art.

Condensation of 2-aminopyridines (formula VII) with diethyl ethoxymethylenemalonate (formula IX) to produce the esters of formula IV is well-documented in the literature (see prior art section above and, in particular, U.S. Pat. 3,585,198, J. Chem. Soc. (C), 2735 (1971), J. Org. Chem., 33, 3015 (1968), Arzneim.-Forsch., 22, 815 (1972) and J. Amer. Chem. Soc., 70, 3348 (1948), and the references cited therein).

Amide intermediates of formula III may be obtained by treatment of the esters of formula IV with liquid ammonia, ammonium hydroxide or a solution of ammonia in a (lower)alkanol (e.g. methanol or ethanol) optionally containing sodium methoxide as a catalyst. The reaction is conveniently carried out in a sealed vessel at steam bath temperature. When concentrated ammonium hydroxide is used, good results have also been achieved at room temperature for one to two days without the necessity of either heat or a sealed vessel.

The amide intermediates of formula III may be converted to the nitriles of formula II by use of a dehydrating agent such as phosphorus pentoxide, thionyl chloride, p-toluenesulfonyl chloride:pyridine or, most preferably, phosphorus oxychloride. Dehydration is accomplished at elevated temperatures, most preferably under reflux conditions.

The acrylate starting materials of formula VI may be prepared by condensing approximately equimolar amounts of a 2-aminopyridine compound of formula VII with ethyl ethoxymethylenecyanoacetate in the presence or absence of an inert organic solvent, e.g. an aromatic hydrocarbon such as toluene. The reaction is preferably carried out at elevated temperatures, e.g. 100° C. Some examples of the acrylates of formula VI (i.e. when the pyridine ring is unsubstituted or substituted at the 3-, 4- or 6-position by methyl) are disclosed by Antaki in *J. Amer. Chem. Soc.*, 80, 3066 (1958) and by Nishigaki, et al. in *J. Heterocycl. Chem.*, 8, 759 (1971).

In using the above-described processes to prepare compounds of formula I in which $R^1$, $R^2$ or $R^4$ contain free hydroxy, amino or carboxyl groups, it is of course understood that such groups will be protected by suitable known protecting groups during the reaction steps beginning with the basic 2-aminopyridine starting materials through the formation of the final tetrazoles. The protecting group(s) may then be removed by methods known per se to give the desired products having the unprotected substituent groups. Amino-substituted compounds may be prepared from the corresponding nitro-substituted product by catalytic hydrogenation. In preparing compounds of formula I where $R^1$, $R^2$ or $R^4$ are (lower)alkylamino or di(lower)alkylamino, the corresponding amino-substituted compound may first be prepared and then alkylated. Alternatively, the dialkylamino-substituted compounds can be prepared directly from the appropriate 2-amino-pyridine starting material.

In another aspect of the present invention, there is provided a method of inhibiting or preventing the symptoms of an allergic reaction such as allergic bronchial asthma or allergic rhinitis in a mammal susceptible to such a reaction which comprises administering to said mammal a prophylactically effective dose of a compound of formula I or a pharmaceutically acceptable salt thereof.

The compounds of the present invention may be administered either as individual therapeutic agents or as mixtures with other therapeutic agents. They may be administered alone but are generally administered in the form of pharmaceutical compositions, i.e. mixtures of the active agents with suitable pharmaceutical carriers or diluents. Examples of such compositions include tablets, lozenges, capsules, powders, aerosol sprays, aqueous or oily suspensions, syrups, elixers and aqueous solutions. The compounds are preferably administered orally, but may also be administered by inhalation, injection, instillation or by implantation for controlled drug release from a solid carrier reservoir.

The nature of the pharmaceutical composition and the pharmaceutical carrier or diluent will, of course, depend on the desired route of administration. For example, oral compositions may be in the form of tablets or capsules and may contain conventional excipients such as binding agents (e.g. syrup, acacia, gelatin, sorbitol, tragacanth or polyvinylpyrrolidone), fillers (e.g. lactose, sugar, maize-starch, calcium phosphate, sorbitol or glycine), lubricants (e.g. magnesium stearate, talc, polyethylene glycol, or silica), disintegrants (e.g. starch) or wetting agents (e.g. sodium lauryl sulfate). Oral liquid preparations may be in the form of aqueous or oily suspensions, solutions, emulsions, syrups, elixers, etc. or may be presented as a dry product for reconstitution with water or other suitable vehicle before use. Such liquid preparations may contain conventional additives such as suspending agents, flavoring agents, diluents or emulsifying agents. For parenteral administration, inhalation or installation, solutions or suspensions of a compound of formula I with conventional pharmaceutical vehicles may be employed, e.g. as an aerosol spray for inhalation, as an aqueous solution for intravenous injection or instillation, or as an oily suspension for intramuscular injection. The compounds may also be administered by means of inhalers or other devices which permit the active compounds in the form of dry powders to come into direct contact with the lungs.

The compounds of the present invention or pharmaceutical compositions thereof may be administered to human allergic patients in single oral doses of approximately 0.05–500 mg. of active ingredient and multiple oral doses totalling up to about 1000 mg./day of active ingredient. When administered by inhalation or installation, lower doses are generally given, i.e. on the order of about 0.1 of the normal oral dosage for the particular compound in question. These values are illustrative only, however, and the physician of course will ultimately determine the dosage most suitable for a particular patient on the basis of factors such as age, weight, severity of the symptoms and the particular agent to be administered.

The reagin-mediated rat Passive Cutaneous Anaphylaxis (PCA) screening test (see description, for example, in U.S. Pat. No. 4,082,751) indicates that the compounds of formula I are highly potent antiallergy agents.

The following examples are provided solely for the purpose of illustrating preparation of representative compounds of the present invention and are not to be construed as limitations of the invention. All temperatures referred to below are in degrees Centigrade. "Skellysolve B" is a petroleum ether fraction of b.p. 60°–68° C. consisting essentially of n-hexane ("Skellysolve" is a trade name of the Skelly Oil Co.)

EXAMPLE 1

8,9,10,11-Tetrahydro-3-(1H-tetrazol-5-yl)-4H-pyrimido[2,1-a]isoquinol-4-one

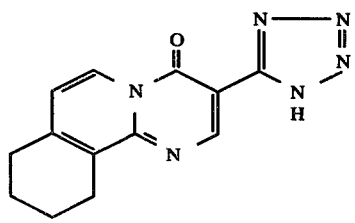

A. Ethyl 2-Cyano-3-(5,6,7,8-tetrahydro-1-isoquinolylamino)-acrylate

A solution of 1-amino-5,6,7,8-tetrahydroisoquinoline [2.96 g., 0.02 mole; E. Ochiai and Y. Kawazoe, Pharm. Bull. (Tokyo), 5, 606 (1957)] and ethyl ethoxymethylenecyanoacetate (3.38 g., 0.02 mole) in toluene (8 ml.) was heated by means of an oil bath maintained at 105° C. for 15 minutes. The cooled solution was poured into Skellysolve B (175 ml.) with good stirring. The mixture was triturated and cooled with an ice bath. The mixture was filtered and the collected gummy solid recrystallized from cyclohexane to give the title compound (4.1 g., 75%), m.p. 116°-120° C. The product was recrystallized from cyclohexane to give analytical material, m.p. 121°-123° C.

Anal. Calc'd. for $C_{15}H_{17}N_3O_2$: C, 66.40; H, 6.32; N, 15.49. Found: C, 66.44; H, 6.26; N, 15.44.

B.

8,9,10,11-Tetrahydro-3-(1H-tetrazol-5-yl)-4H-pyrimido-[2,1-a]isoquinol-4-one

Aluminum chloride (2.05 g., 0.0154 mole) was added to cold (−30° C.) tetrahydrofuran (75 ml.). Sodium azide was added and the mixture heated under reflux for 40 minutes. Ethyl 2-cyano-3-(5,6,7,8-tetrahydro-1-isoquinolylamino)-acrylate (3.33 g., 0.0123 mole) was added and the mixture heated under reflux for 20 hours. The cooled mixture was diluted with water (100 ml.) and acidified with concentrated hydrochloric acid. The precipitate was collected, washed with water, dried and recrystallized from 2-methoxyethanol to give the title compound (0.625 g., 19%), m.p. 290°-292° C. (decomp.).

Anal. Calc'd for $C_{13}H_{12}N_6O$: C, 58.20; H, 4.51; N, 31.33. Found: C, 58.07; H, 4.60; N, 31.06.

EXAMPLE 2

Following the general procedure of Example 1, the following compounds may be prepared by use of the appropriate starting materials.

| $R^1$ | $R^2$ | $R^3$ | $R^4$ |
|---|---|---|---|
| H | $CO_2H$ | $(CH_2)_4$ | |
| $CH_3$ | H | " | " |
| H | $CH_3(CH_2)_3O$ | " | " |
| $t$-$C_4H_9$ | H | " | " |
| $C_6H_5$ | H | " | " |
| H | $C_2H_5O$ | " | " |
| H | Cl | " | " |
| H | $C_6H_5CH_2$ | " | " |
| H | OH | " | " |
| H | 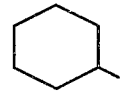 | " | " |
| H | 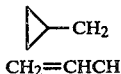 | " | " |
| H | $CH_2=CHCH_2$ | " | " |
| H | $CH\equiv CCH_2$ | " | " |
| H | $CH_3OCH_2CH_2$ | " | " |
| H | $CH_2=CHCH_2O$ | " | " |
| H | 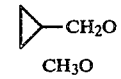 | " | " |
| $CH_3$ | $CH_3O$ | " | " |
| F | H | " | " |
| $n$-$C_4H_9$ | $C_2H_5O$ | " | " |
| $C_6H_5$ | $CH_3O$ | " | " |
| H | $CH_3OCH_2CH_2O$ | " | " |
| H | $CF_3$ | " | " |
| H | $HOCH_2$ | " | " |
| H | $CH_3S$ | " | " |
| H | $NH_2$ | " | " |
| H | $NO_2$ | " | " |
| H | 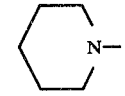 | " | " |
| H | $CH_3NH$ | " | " |
| H | $(CH_3)_2N$ | " | " |
| H | 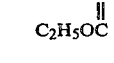 | " | " |

-continued

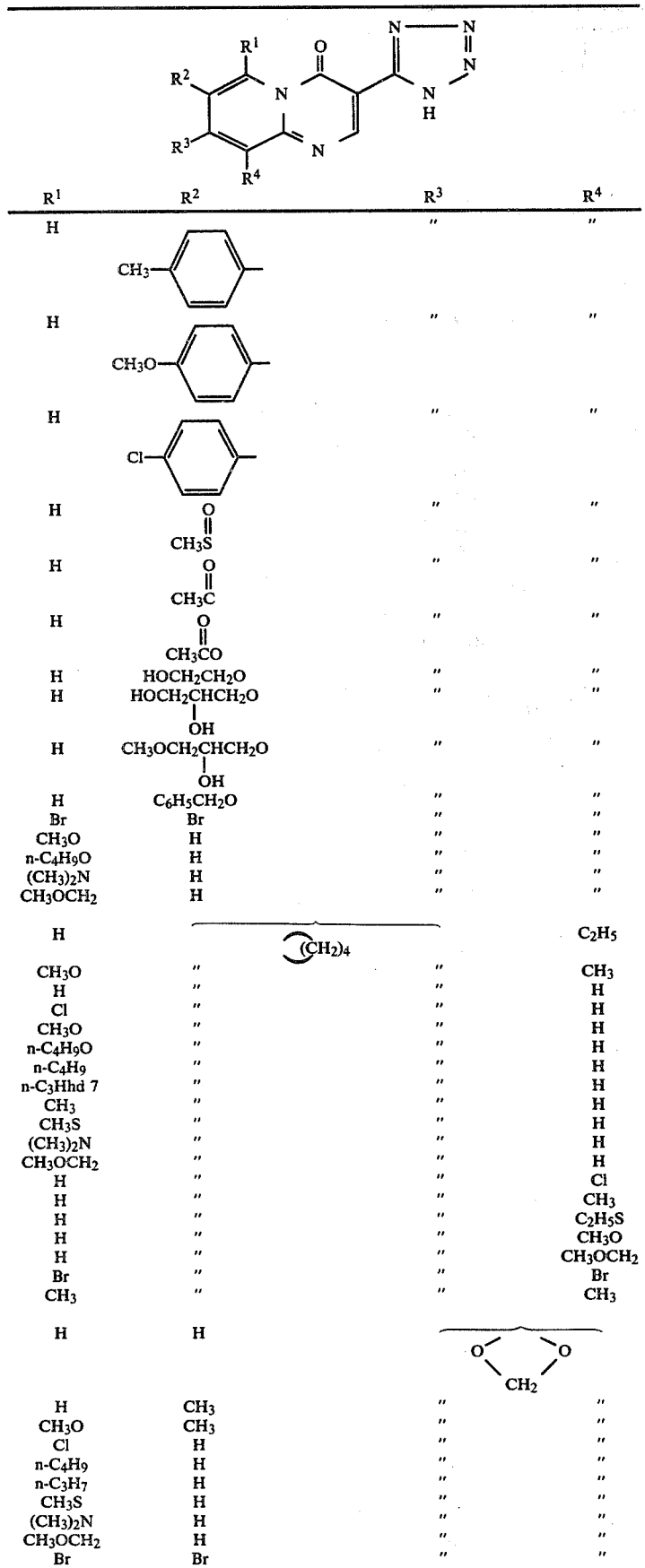

| R¹ | R² | R³ | R⁴ |
|---|---|---|---|
| H | 4-CH₃-C₆H₄- | " | " |
| H | 4-CH₃O-C₆H₄- | " | " |
| H | 4-Cl-C₆H₄- | " | " |
| H | CH₃S(O)- | " | " |
| H | CH₃C(O)- | " | " |
| H | CH₃CO-O- | " | " |
| H | HOCH₂CH₂O | " | " |
| H | HOCH₂CH(OH)CH₂O | " | " |
| H | CH₃OCH₂CH(OH)CH₂O | " | " |
| H | C₆H₅CH₂O | " | " |
| Br | Br | " | " |
| CH₃O | H | " | " |
| n-C₄H₉O | H | " | " |
| (CH₃)₂N | H | " | " |
| CH₃OCH₂ | H | " | " |
| H | —(CH₂)₄— | | C₂H₅ |
| CH₃O | " | " | CH₃ |
| H | " | " | H |
| Cl | " | " | H |
| CH₃O | " | " | H |
| n-C₄H₉O | " | " | H |
| n-C₄H₉ | " | " | H |
| n-C₃H₇ | " | " | H |
| CH₃ | " | " | H |
| CH₃S | " | " | H |
| (CH₃)₂N | " | " | H |
| CH₃OCH₂ | " | " | H |
| H | " | " | Cl |
| H | " | " | CH₃ |
| H | " | " | C₂H₅S |
| H | " | " | CH₃O |
| H | " | " | CH₃OCH₂ |
| Br | " | " | Br |
| CH₃ | " | " | CH₃ |
| H | H | —O-CH₂-O— | |
| H | CH₃ | " | " |
| CH₃O | CH₃ | " | " |
| Cl | H | " | " |
| n-C₄H₉ | H | " | " |
| n-C₃H₇ | H | " | " |
| CH₃S | H | " | " |
| (CH₃)₂N | H | " | " |
| CH₃OCH₂ | H | " | " |
| Br | Br | " | " |

-continued

[Structure: pyrido[1,2-a]pyrimidin-4-one with R¹, R², R³, R⁴ substituents and a tetrazolyl group]

| R¹ | R² | R³ | R⁴ |
|---|---|---|---|
| CH₃ | CH₃ | " | " |
| H | CH₃O | " | " |
| H | n-C₄H₉ | " | " |
| H | C₂H₅S | " | " |
| H | —O—CH₂—O— (methylenedioxy across R²–R³) | | H |
| CH₃ | " | " | H |
| H | " | " | CH₃ |
| CH₃O | " | " | CH₃ |
| Cl | " | " | H |
| n-C₄H₉O | " | " | H |
| n-C₄H₉ | " | " | H |
| CH₃ | " | " | H |
| CH₃S | " | " | H |
| (CH₃)₂N | " | " | H |
| CH₃OCH₂ | " | " | H |
| H | " | " | Cl |
| H | " | " | C₂H₅S |
| H | " | " | CH₃O |
| H | " | " | CH₃OCH₂ |
| Br | " | " | Br |
| H | H | —(CH₂)₃— (across R³–R⁴) | |
| H | H | —(CH₂)₅— (across R³–R⁴) | |
| H | —(CH₂)₃— (across R²–R³) | | H |
| H | —(CH₂)₅— (across R²–R³) | | H |
| H | Cl | —(CH₂)₃— (across R³–R⁴) | |
| H | CH₃O | " | " |
| H | CH₃ | " | " |
| H | n-C₃H₇ | " | " |
| H | n-C₄H₉O | " | " |
| CH₃ | H | " | " |
| H | CH₃S | " | " |
| H | (CH₃)₂N | " | " |
| H | CH₃OCH₂ | " | " |
| n-C₄H₉ | H | " | " |
| CH₃O | H | " | " |
| Br | Br | " | " |
| Cl | H | " | " |
| Cl | H | —(CH₂)₅— (across R³–R⁴) | |
| CH₃ | H | " | " |
| CH₃S | H | " | " |
| CH₃OCH₂ | H | " | " |
| n-C₄H₉ | H | " | " |
| (CH₃)₂N | H | " | " |
| Br | Br | " | " |
| H | CH₃ | " | " |
| H | CH₃S | " | " |
| CH₃ | CH₃ | " | " |
| H | CH₃O | " | " |
| H | —(CH₂)₃— (across R²–R³) | | Cl, Cl |
| CH₃ | " | " | CH₃ |
| CH₃O | " | " | H |
| n-C₄H₉O | " | " | H |
| CH₃S | " | " | H |
| H | " | " | n-C₄H₉ |
| (CH₃)₂N | " | " | H |

-continued

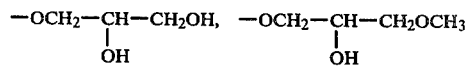

| $R^1$ | $R^2$ | $R^3$ | $R^4$ |
|---|---|---|---|
| H | " | " | $CH_3OCH_2$ |
| H | " | " | $CH_3O$ |
| Br | " | " | Br |
| $CH_3$ | $(CH_2)_5$ | | $CH_3$ |
| $CH_3S$ | " | " | H |
| $n-C_4H_9$ | " | " | H |
| $CH_3OCH_2$ | " | " | H |
| $(CH_3)_2N$ | " | " | H |
| $n-C_4H_9O$ | " | " | H |
| H | " | " | $CH_3O$ |
| H | " | " | $CH_3S$ |
| H | " | " | $CH_3OCH_2$ |
| H | " | " | Cl |
| Br | " | " | Br |

EXAMPLE 3

8,9,10,11-Tetrahydro-3-(1H-tetrazol-5-yl)-4H-pyrimido[2,1-a]-isoquinol-4-one, Sodium Salt Approximately one equivalent of 1N NaOH is added to a stirred mixture of 8,9,10,11-tetrahydro-3-(1H-tetrazol-5-yl)-4H-pyrimido[2,1-a]isoquinol-4-one in water. Upon lyophilization there is obtained the title salt.

Replacement of the 8,9,10,11-tetrahydro-3-(1H-tetrazol-5-yl)-4H-pyrimido[2,1-a]isoquinol-4-one in the above procedure with an equimolar weight of the products produced in Example 2 gives the corresponding sodium salts for each of the indicated compounds.

Replacement of the sodium hydroxide in the above procedure with other bases, e.g. KOH, Ca(OH)$_2$, Mg(OH)$_2$ or NH$_4$OH, gives the corresponding base addition salts.

Reaction of the compounds of Examples 1 and 2 with an equivalent weight of ethanolamine, ethylenediamine, diethanolamine, triethanolamine or tris(hydroxymethyl)-aminomethane gives the corresponding amine salts for each of the indicated compounds.

The compounds of Examples 1 and 2 may be converted to their acid addition salts by addition of a stoichiometric amount of a suitable organic or inorganic acid, e.g. HCl, HBr, HI, H$_3$PO$_4$ or CH$_3$COOH.

We claim:

1. A compound of the formula

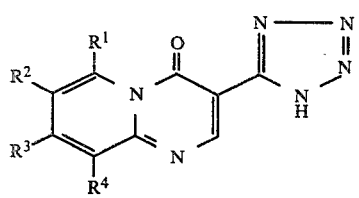

wherein $R^2$ and $R^3$ or $R^3$ and $R^4$ when taken together are methylenedioxy or

in which n is 3, 4 or 5 and the remaining available $R^1$, $R^2$ and $R^4$ substituents are each independently hydrogen, halogen, (lower)alkyl, (lower)alkoxy, (lower)alkoxy-(lower)alkyl, [—O—(lower)alkenyl,

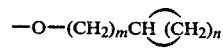

in which m is 0 or an integer from 1 to 6 and n is an integer from 2 to 7, —OCH$_2$(CH$_2$)$_x$O(CH$_2$)$_y$CH$_3$ in which x and y are each independently 0 or an integer from 1 to 6, CF$_3$, hydroxy, hydroxymethyl,] (lower)alkylthio, [amino, nitro,

in which r is 4 or 5, (lower)alkylamino,] or di(lower)alkylamino, [carboxyl, —CO$_2$—(lower)alkyl, phenyl, phenyl substituted by one or two (lower)alkyl, (lower)alkoxy or halogen radicals, benzyl, (lower)alkylsulfinyl, R$^c$—CO— in which R$^c$ is (lower)alkyl, R$^c$—COO— in which R$^c$ is (lower)alkyl, —O(CH$_2$)$_k$OH in which k is an integer from 2 to 6, $$-OCH_2-\underset{OH}{CH}-CH_2OH, \quad -OCH_2-\underset{OH}{CH}-CH_2OCH_3$$

or —OCH$_2$C$_6$H$_5$,] with the proviso that $R^1$ and $R^2$ may not both be tertiary alkyl or tertiary alkoxy groups, or a pharmaceutically acceptable salt thereof.

2. A compound according to claim 1 wherein $R^2$ and $R^3$ or $R^3$ and $R^4$ when taken together are methylenedioxy.

3. A compound according to claim 1 wherein $R^2$ and $R^3$ or $R^3$ and $R^4$ when taken together are

in which n is 3, 4 or 5.

4. A compound according to claim 3, wherein $R^3$ and $R^4$ taken together are

in which n is 3, 4 or 5.

5. A compound of the formula

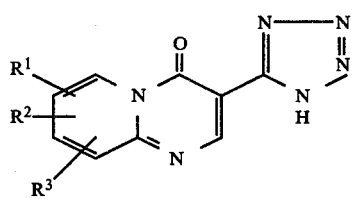

wherein any two of $R^1$, $R^2$ and $R^3$ at positions 7 and 8 or 8 and 9 of the pyrido pyrimidine ring system when taken together represent methylenedioxy or

in which n is 3, 4 or 5 and the remaining available $R^1$, $R^2$ or $R^3$ substituent is hydrogen, halogen, (lower)alkyl, (lower)alkoxy, (lower)alkoxy-(lower)alkyl, [—O—(-lower)alkenyl,

in which m is 0 or an integer from 1 to 6 and n is an integer from 2 to 7, —OCH$_2$(CH$_2$)$_x$O(CH$_2$)$_y$CH$_3$ in which x and y are each independently 0 or an integer from 1 to 6, CF$_3$, hydroxy, hydroxymethyl,] (lower)alkylthio, [amino, nitro,

in which r is 4 or 5, (lower)alkylamino,] or di(lower)alkylamino, [carboxyl, —CO—(lower)alkyl, phenyl, phenyl substituted by one or two (lower)alkyl, (lower)alkoxy or halogen radicals, benzyl, (lower)alkylsulfinyl, $R^c$—CO— in which $R^c$ is (lower)alkyl, $R^c$—COO— in which $R^c$ is (lower)alkyl, —O(CH$_2$)$_k$OH in which k is an integer from 2 to 6,

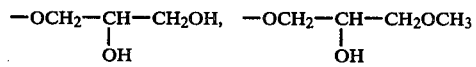

or —OCH$_2$C$_6$H$_5$,] or a pharmaceutically acceptable salt thereof.

6. A compound according to claim 5 wherein two of $R^1$, $R^2$ and $R^3$ at positions 7 and 8 or 8 and 9 of the pyrido-[1,2-a]pyrimidine ring system when taken together are methylenedioxy.

7. A compound according to claim 5 wherein two of $R^1$, $R^2$ and $R^3$ at positions 7 and 8 or 8 and 9 of the pyrido-[1,2-a]pyrimidine ring system when taken together are

in which n is 3, 4 or 5.

8. A compound according to claim 7 wherein two of $R^1$, $R^2$ and $R^3$ at positions 8 and 9 of the pyrido[1,2-a]pyrimidine ring system represent

in which n is 3, 4 or 5.

9. A compound of the formula

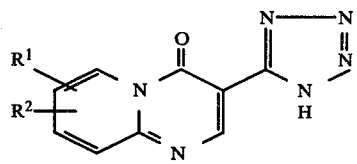

wherein $R^1$ and $R^2$ when taken together at positions 7 and 8 or 8 and 9 of the pyrido[1,2-a]pyrimidine ring system are methylenedioxy or

in which n is 3, 4 or 5, or a pharmaceutically acceptable salt thereof.

10. A compound according to claim 9 wherein $R^1$ and $R^2$ are

in which n is 3, 4 or 5.

11. A compound of the formula

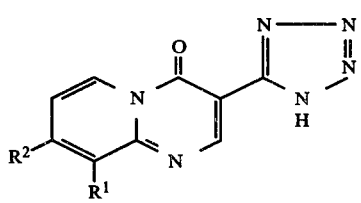

wherein $R^1$ and $R^2$ when taken together at positions 8 and 9 of the pyrido[1,2-a]pyrimidine ring system are methylenedioxy or

in which n is 3, 4 or 5, or a pharmaceutically acceptable salt thereof.

12. A compound of the formula

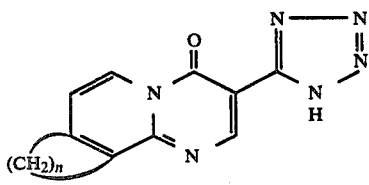
wherein n is 3, 4 or 5, or a pharmaceutically acceptable salt thereof.
13. A compound of the formula
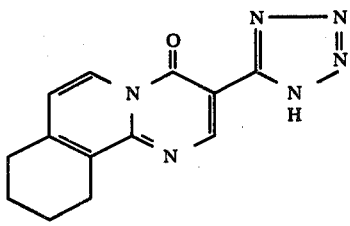
or a pharmaceutically acceptable salt thereof.
* * * * *

UNITED STATES PATENT AND TRADEMARK OFFICE
CERTIFICATE OF CORRECTION

PATENT NO. : 4,209,620
DATED : June 24, 1980
INVENTOR(S) : Peter F. Juby

It is certified that error appears in the above-identified patent and that said Letters Patent are hereby corrected as shown below:

In Claim 1, lines 33-41, delete the bracketed subject matter.

In Claim 1, lines 42-47, delete the bracketed subject matter.

In Claim 1, lines 48-59, delete the bracketed subject matter.

In Claim 5, lines 33-43, delete the bracketed subject matter.

In Claim 5, lines 44-49, delete the bracketed subject matter.

In Claim 5, lines 50-61, delete the bracketed subject matter.

Signed and Sealed this

Twenty-sixth Day of August 1980

[SEAL]

Attest:

SIDNEY A. DIAMOND

Attesting Officer

Commissioner of Patents and Trademark